(12) United States Patent
Froissard et al.

(10) Patent No.: US 12,353,061 B2
(45) Date of Patent: Jul. 8, 2025

(54) UNIVERSAL-FIT EYEGLASSES

(71) Applicant: 3M INNOVATIVE PROPERTIES COMPANY, St. Paul, MN (US)

(72) Inventors: Laurent Froissard, Cottage Grove, MN (US); Laurel A. Alvarez, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 347 days.

(21) Appl. No.: 18/026,491

(22) PCT Filed: Sep. 15, 2021

(86) PCT No.: PCT/IB2021/058419
§ 371 (c)(1),
(2) Date: Mar. 15, 2023

(87) PCT Pub. No.: WO2022/074486
PCT Pub. Date: Apr. 14, 2022

(65) Prior Publication Data
US 2023/0393415 A1    Dec. 7, 2023

Related U.S. Application Data

(60) Provisional application No. 63/104,352, filed on Oct. 22, 2020, provisional application No. 63/089,666, filed on Oct. 9, 2020.

(51) Int. Cl.
*G02C 5/12* (2006.01)
(52) U.S. Cl.
CPC ............. *G02C 5/126* (2013.01); *G02C 5/122* (2013.01)

(58) Field of Classification Search
CPC .......................... G02C 5/12–18; A61F 9/026
See application file for complete search history.

(56) References Cited

U.S. PATENT DOCUMENTS

| | | | |
|---|---|---|---|
| 4,704,015 A | 11/1987 | Grendol et al. | |
| 5,345,616 A * | 9/1994 | Wiedner | G02C 5/143 351/87 |
| 5,555,038 A * | 9/1996 | Conway | G02C 5/126 351/44 |
| 5,790,230 A | 8/1998 | Sved | |
| 5,825,453 A | 10/1998 | Baragar et al. | |
| RE36,048 E | 1/1999 | Schmolz et al. | |
| 6,085,748 A | 7/2000 | Sword et al. | |
| 6,106,117 A | 8/2000 | Huang Lin | |
| 6,340,228 B1 | 1/2002 | Cummings et al. | |
| 6,401,716 B1 | 6/2002 | Sword et al. | |

(Continued)

FOREIGN PATENT DOCUMENTS

JP          6599125 B2    10/2019

OTHER PUBLICATIONS

International Search Report for PCT International Application No. PCT/IB2021/058419, mailed on Dec. 14, 2021, 3 pages.

*Primary Examiner* — Cara E Rakowski
(74) *Attorney, Agent, or Firm* — Kenneth B. Wood (57) ABSTRACT

Eyeglasses with a flare-nose aperture in which is positioned a nosepiece that has left and right nosepads each comprising a generally U-shaped cross section and being made of a compliant material wherein the flare-nose aperture is defined by at least abridge portion of a frame and laterally-inward terminal edges of left and right lenses.

17 Claims, 10 Drawing Sheets

(56) References Cited

U.S. PATENT DOCUMENTS

| | | |
|---|---|---|
| 7,425,065 B2 | 9/2008 | Wang |
| 7,631,967 B1 | 12/2009 | Huang |
| 8,365,732 B2 | 2/2013 | Johnstone |
| 9,409,056 B2 | 8/2016 | Lee |
| 9,946,090 B2 | 4/2018 | Goodger |
| 10,073,284 B2 | 9/2018 | Sheldon |
| 10,185,157 B2 | 1/2019 | Lee |
| 10,330,949 B2 | 6/2019 | Sheldon et al. |
| 2012/0050666 A1 | 3/2012 | Havens-Olmstead |
| 2012/0062832 A1* | 3/2012 | Stanley .................... G02C 5/12 351/136 |
| 2018/0107019 A1 | 4/2018 | Chen |
| 2019/0107732 A1* | 4/2019 | Canales .................. G02C 7/02 |
| 2019/0314203 A1 | 10/2019 | D'Orazio |
| 2019/0346689 A1 | 11/2019 | Canales et al. |

* cited by examiner

UNIVERSAL-FIT EYEGLASSES

CROSS REFERENCE TO RELATED APPLICATIONS

This application is a national stage filing under 35 U.S.C. 371 of PCT/IB2021/058419, filed 15 Sep. 2021, which claims the benefit of U.S. Provisional Patent Application No. 63/089,666, filed 9 Oct. 2020 and which claims the benefit of U.S. Provisional Patent Application No. 63/104,352, filed 22 Oct. 2020 the disclosure of which is incorporated by reference in its/their entirety herein.

BACKGROUND

Eyeglasses are typically worn for extended periods of time, whether for vision correction, protection from physical hazards, and/or protection from sunlight. The comfort with which such eyeglasses fit is thus of importance.

SUMMARY

In broad summary, herein are disclosed eyeglasses comprising a flared nose-aperture in which is positioned a nosepiece comprising left and right elongate nosepads each comprising a generally U-shaped cross-section. These and other aspects will be apparent from the detailed description below. In no event, however, should this broad summary be construed to limit the claimable subject matter, whether such subject matter is presented in claims in the application as initially filed or in claims that are amended or otherwise presented in prosecution.

Like reference numbers in the various figures indicate like elements. Some elements may be present in identical or equivalent multiples; in such cases only one or more representative elements may be designated by a reference number but it will be understood that such reference numbers apply to all such identical elements. Unless otherwise indicated, all figures and drawings in this document are not to scale and are chosen for the purpose of illustrating different embodiments of the invention. In particular the dimensions of the various components are depicted in illustrative terms only, and no relationship between the dimensions of the various components should be inferred from the drawings, unless so indicated.

As used herein as a modifier to a property or attribute, the term "generally", unless otherwise specifically defined, means that the property or attribute would be readily recognizable by a person of ordinary skill but without requiring a high degree of approximation (e.g., within +/−20% for quantifiable properties). The term "substantially", unless otherwise specifically defined, means to a high degree of approximation (e.g., within +/−10% for quantifiable properties). The term "essentially" means to a very high degree of approximation (e.g., within plus or minus 2% for quantifiable properties. The term "configured to" and like terms is at least as restrictive as the term "adapted to", and requires actual design intention to perform the specified function rather than mere physical capability of performing such a function. All references herein to numerical values (e.g. dimensions, ratios, and so on), unless otherwise noted, are understood to be calculable as average values derived from an appropriate number of measurements of the parameter(s) in question.

Figure 2:
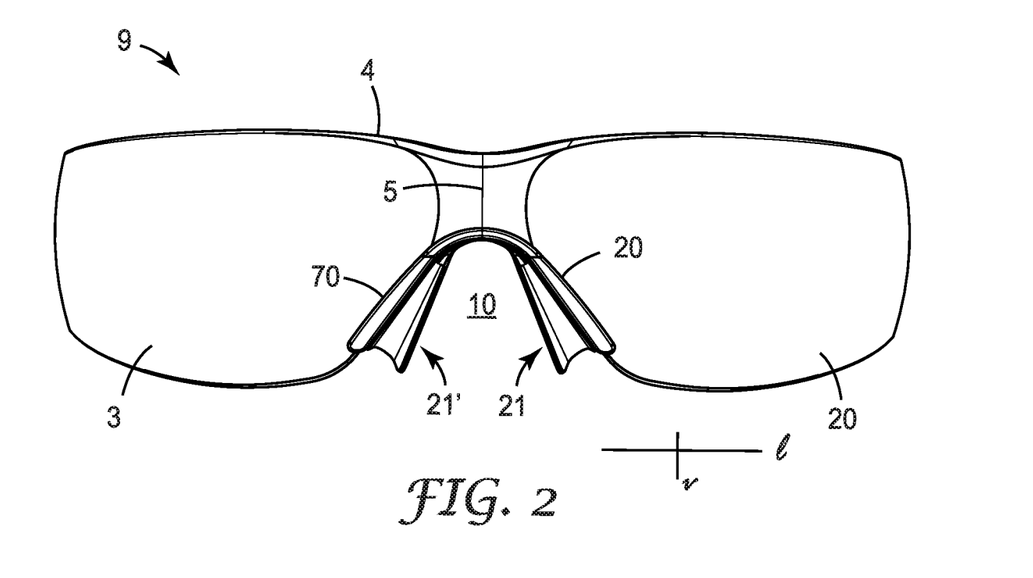
FIG. 2 is a front view of the eyeglasses of FIG. 1, with the temple arms of the eyeglasses omitted.
Figure 5:
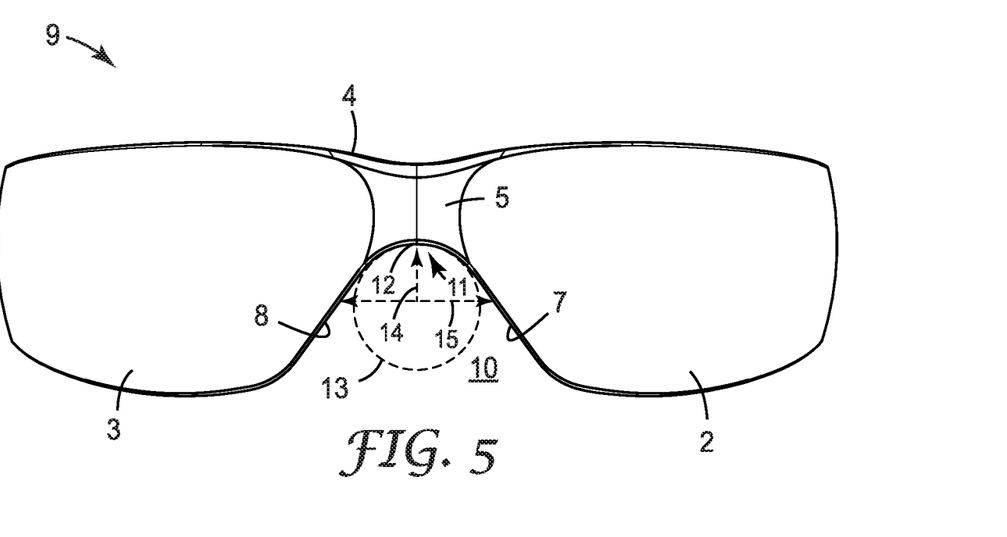
FIG. 5 is a front view of the eyeglasses of FIG. 2, with various parameters indicated thereon.

Vertical directions such as up and down, lateral directions such as right and left, and forward (generally away from the wearer's face) and rearward (generally toward the wearer's face) directions, will all be understood to apply to a pair of eyeglasses as conventionally fitted on the head of a human user with the head in an upright condition. For convenience, the vertical (up-down) axis (v) and lateral (left-right) axis (l) of an exemplary pair of eyeglasses are indicated in FIG. 2. Orientations such as e.g. laterally-inward, laterally-outward, and so on, are to be interpreted as "generally" laterally inward or outward, and do not require that the item must be e.g. oriented exactly along the lateral axis of the eyeglasses. Thus for example, laterally-inward facing edges 7 and 8 of lenses 2 and 3 as shown in FIG. 5, face somewhat downward as well as facing laterally inward.

DETAILED DESCRIPTION

Figure 1:
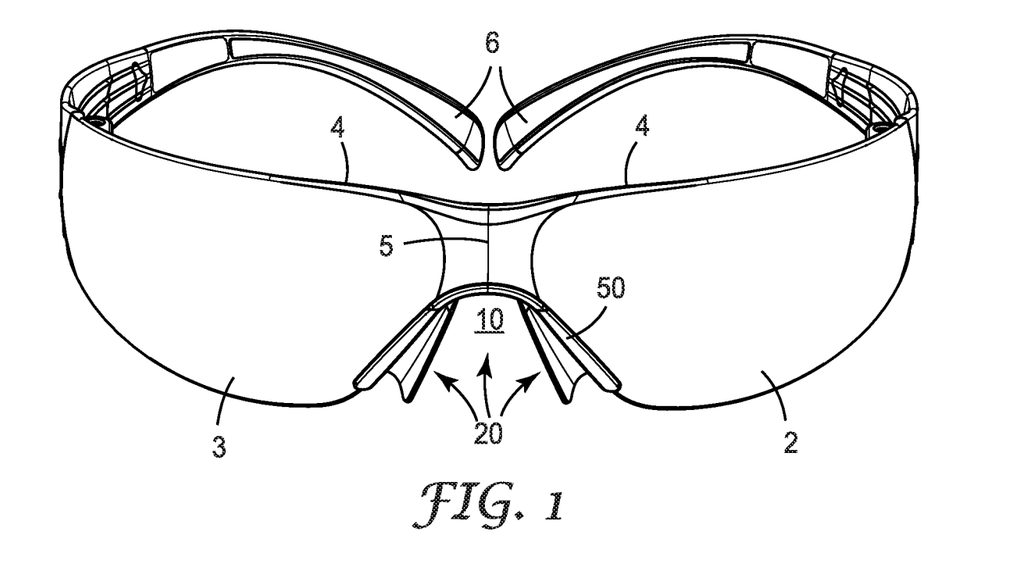
FIG. 1 is a front view of an exemplary pair of eyeglasses comprising an exemplary nosepiece as disclosed herein.
Figure 3:
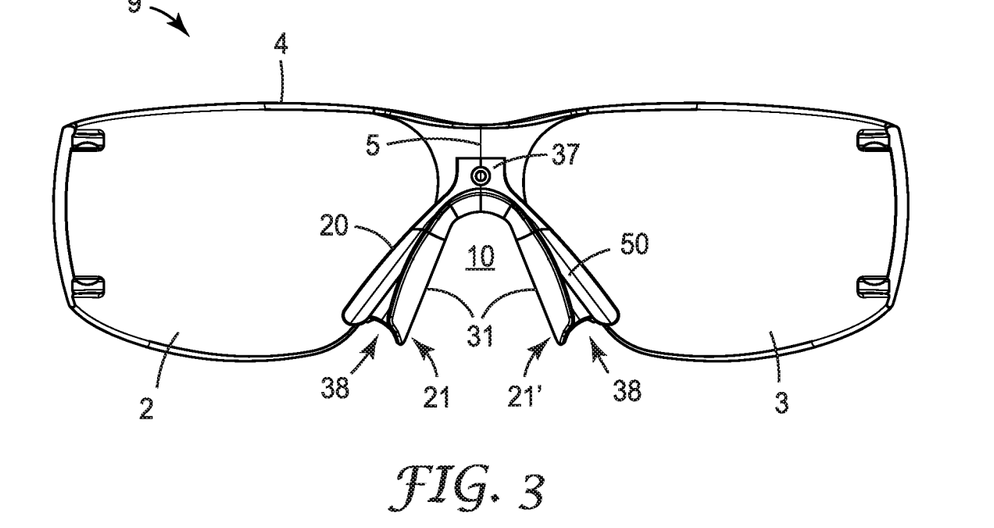
FIG. 3 is a rear view of the eyeglasses of FIG. 2.

Disclosed herein is a set (often referred to as a "pair") of eyeglasses 1. Eyeglasses 1 typically comprise left lens 2 and right lens 3, two temple arms 6, and a frame 4, as shown in exemplary manner in FIGS. 1-3. (FIGS. 2 and 3 are front and rear views with the temple arms omitted so that other components can be more easily seen.) In some embodiments a frame 4 may partially or completely surround (and thus hold from all sides) each lens 2 and 3. However, in some embodiments a frame 4 may only partially surround each lens. In some such embodiments a frame 4 may comprise mainly a bridge portion 5 that is centrally located (positioned directly over the nose of the wearer when the glasses are worn) and that connects the two lenses to each other. Such a design may sometimes include a support beam that extends laterally outward from the bridge portion along at least a portion of the upper edge of the lenses, as in FIGS. 1 and 2 herein. Such arrangements are common e.g. in some integrated lens/frame designs (such as the eyeglasses available from 3M Company, St. Paul MN under the trade designation SECURE-FIT 400 (SF400)). It is thus emphasized that the term "frame" as used herein encompasses not only a frame that completely or partially surrounds the lenses of eyeglasses, but also a frame that consists mainly or only of a bridge portion between the lenses of eyeglasses, as in the exemplary eyeglasses depicted herein. In some instances, portions of a frame may extend along laterally-inward edges of lenses 2 and 3. In cases in which portions of a frame extend along the laterally-inward edges, the frame itself will define the laterally-inward edges of the lenses for the purpose of evaluating certain parameters of the eyeglasses, as discussed in detail later herein.

Eyeglasses 1 comprises a nose-aperture (nasal slot) 10 as shown in exemplary embodiment in the front view of FIG. 2 and the rear view of FIG. 3, to accommodate the wearer's nose when the glasses are worn. Eyeglasses 1 comprise a nosepiece 20 that is positioned in nose-aperture 10. As disclosed herein, nosepiece 20 is a separately-made piece that is attached, permanently or detachably, to eyeglasses 1, rather than being an integral component of eyeglasses 1. In many convenient embodiments, nosepiece 20 may be attached to eyeglasses 1 at least in part by way of a base 37 of nosepiece 20 being attached to bridge portion of frame 4, as in the exemplary embodiment depicted in FIG. 3. (The exemplary eyeglasses shown in these Figures comprise a bridge portion 5 that is opaque, so that base 37 of nosepiece 20 is visible in the rear view of FIG. 3 but is not visible in the front view of FIG. 2.)

Figure 4:
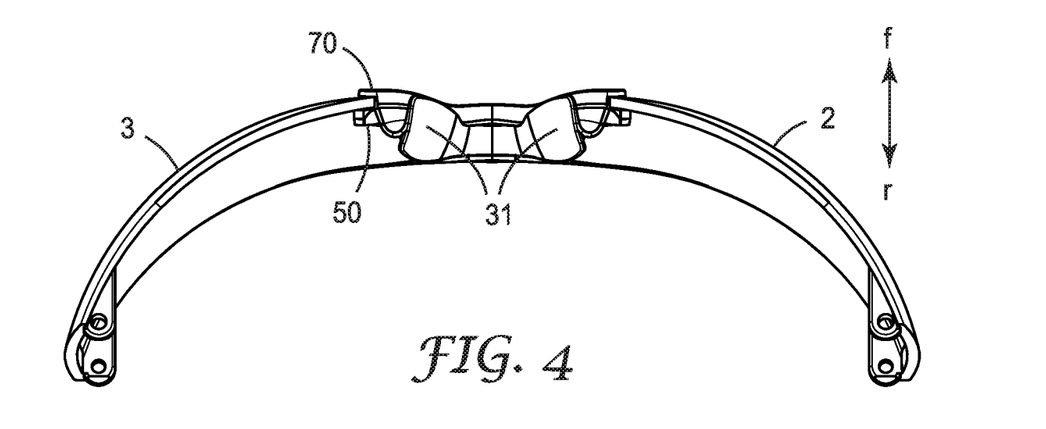
FIG. 4 is a bottom view of the eyeglasses of FIG. 2.

Nosepiece 20 may often be generally Y-shaped as evident in FIGS. 2 and 3, with left and right elongate arms that respectively comprise first and second (left and right) elongate nosepads 21 and 21', as indicated in FIG. 2. (Typically, nosepiece 20 will be left-right symmetrical with nosepads 21 and 21' being mirror images of each other, as in the FIGS. herein.) Nosepads 21 are configured to provide contact surfaces 31 that contact the wearer's nose so as to comfortably support eyeglasses 1, as indicated in FIG. 3 and as shown in the bottom view of FIG. 4.

Nose-aperture 10 is a flared nose-aperture, as defined and discussed in detail later herein. In brief, such an aperture is flared at a greater angle, and is wider (along the lateral direction of the eyeglasses) in locations near the upper boundary of the aperture, than with conventional nose-apertures of eyeglasses in the art. And, nosepads 21 exhibit greater self-adjustability (in particular, a greater range of motion of at least some portions of the nosepads) in comparison to nosepads of the art. This combination of nosepads with greater self-adjustability, and a flared nose-aperture, allows the disclosed eyeglasses to accommodate a greater range of nose widths and shapes. In particular, the disclosed eyeglasses are able to fit well in the presence and in the absence of a facemask. (By a facemask is meant a respirator mask, surgical mask, disposable respirator, N95 mask, cloth mask, or the like, as are often used for infection prevention, for protection against particles in the air, and so on.) This is in contrast to conventional eyeglasses, in which case the space taken up by such a mask on the sides of the wearer's nose can cause conventional eyeglasses to e.g. sit higher on the nose and thus to be less comfortable.

In the art, some eyeglasses have conventionally been fitted with "adjustable" nosepads. Such nosepads are not self-adjustable in the sense used herein but rather are manually adjustable by a wearer (or other person, such as e.g. an optician.) Such nosepads, once adjusted (that is, manually deformed, moved, or otherwise manipulated to a new position, shape, angle, etc.), will remain in that adjusted configuration until they are manually re-adjusted. Thus for eyeglasses with conventionally-adjustable nosepads, adjusting the nosepads to fit properly in the presence of a facemask will cause that when the mask is removed, the nosepads have to be re-adjusted. (In the case of eyeglasses with non-adjustable nosepads, options may be limited in achieving optimum comfort in the presence and absence of a facemask.)

The herein-disclosed eyeglasses comprise nosepads that are self-adjustable and that are able to self-adjust to different nose shapes and sizes and in particular can compensate for the presence or absence of a facemask. By self-adjustable is meant that at least portions of the nosepads are able to deflect (e.g. to expand and contract) so as to change their size and/or shape automatically, and reversibly, in response to the environment, as described in detail later herein. This occurs in response to the shape of the nose and/or the presence of a facemask, without the wearer needing to remove the eyeglasses and manually adjust the nosepads. In fact, the herein-disclosed nosepads are not manually adjustable in the manner described above for conventional adjustable nosepads. Rather, a self-adjustable nosepad as disclosed herein will typically remain in a zero-force, resting condition (typically, in an "expanded" configuration) as discussed in detail later herein, until the nosepad is subjected to a force that may cause at least some portion of the nosepad to deflect. When the force ceases, this portion of the nosepad will return to the resting condition. Again, all this occurs automatically, without the need for any manual adjustment on the part of the wearer.

The combination of nosepads that are self-adjustable over a wide range of displacement, along with installing the nosepads in a flared nose-aperture that allows this wide range of displacement of the nosepads, allows the herein-disclosed eyeglasses to achieve a "universal" fit. That is, the eyeglasses can accommodate a wide range of nose sizes and shapes, and in particular can provide enhanced comfort in the presence or absence of a facemask.

Flared Nose-Aperture

Figure 6:
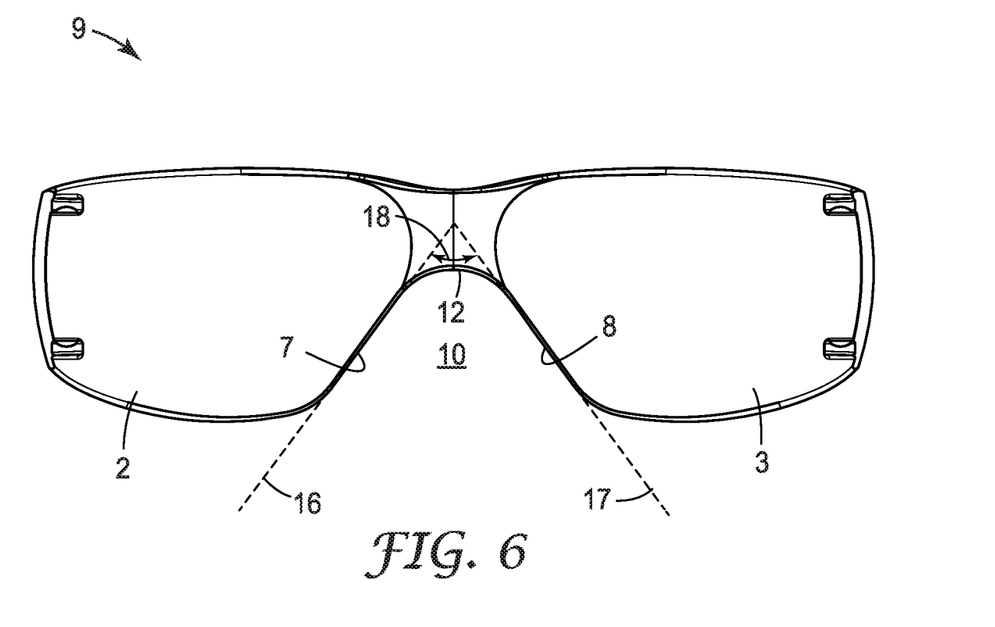
FIG. 6 is a rear view of the eyeglasses of FIG. 3, with various parameters indicated thereon.

The concept of a flared nose-aperture is discussed in regard to FIGS. 5 and 6, which are front and rear views of a set of eyeglasses with the nosepiece (as well as temple arms) omitted so that details of the nose-aperture 10 can be seen. (It will be appreciated that in this particular design, lenses 2 and 3 and frame 4 are all provided as portions of a single, integral, molded piece 9.) For a nose-aperture 10 to be flared in the manner defined herein, all portions of the aperture that are less than 20 mm wide (in lateral width, along the left-right lateral axis of the eyeglasses), must be bounded by surfaces that are oriented at an angle that is at least 30 degrees away from the vertical axis of the eyeglasses. Such surfaces will typically be defined by lower and/or laterally-inward edges of bridge portion 5, and/or by laterally-inward terminal edges of lenses 2 and 3. In various embodiments, all such surfaces may be oriented at least 35, 40 or 45 degrees away from the vertical axis of the eyeglasses.

In some embodiments, any portions of the nose-aperture that are less than 10 mm vertically below the uppermost point 12 of upper boundary 11 of nose-aperture 10, will be bounded by lower and/or laterally-inward edges of the bridge portion and/or by laterally-inward terminal edges of the left or right lenses that are all oriented at an angle that is at least 30 degrees away from a vertical axis of the eyeglasses. In FIG. 5, representative line 15 is located approximately 10 mm below uppermost point 12; thus, all edges of the lenses and/or of the bridge portion that are above this line must meet this angular condition. In various embodiments, all such surfaces may be oriented at least 35, 40 or 45 degrees away from the vertical axis of the eyeglasses.

In some embodiments, a flared nose-aperture 10 may be further characterized by way of a radius of curvature of upper boundary 11. Such a radius of curvature will be evaluated by superimposing a best-fit circle 13 on upper boundary 11 in the manner indicated in FIG. 5; a radius of curvature 14 of circle 13 can then be obtained. In various embodiments, such a radius of curvature may be at least 8, 10, 12 mm; in further embodiments, the radius of curvature may be at most 18, 16 or 14 mm. (In the exemplary design of FIG. 5, the radius of curvature 14 is approximately 10 mm.) A relatively large radius of curvature may enhance the compatibility of the eyeglasses with a facemask, in particular a respirator mask that includes a nasal cushion or seal (which can result in the presence, in the nose region of the mask, of additional layers whose thickness must be taken into account).

In some embodiments, a flared nose-aperture 10 may be further characterized by way of an angle between laterally-inward terminal edges 7 and 8 of left and right lenses 2 and 3. With reference to FIG. 6, such an angle may be measured along portions of edges 7 and 8 that are between 5 and 15 mm vertically below uppermost point 12 of nose-aperture 10. If these portions are substantially linear, the measurement may be performed by superimposing lines 16 and 17 on these portions of the edges as shown in FIG. 6 and measuring angle 18 therebetween. If some curvature or variation is present, a best-fit line may be superimposed that best matches the overall slope of the edges at three points, located 5, 10 and 15 mm vertically below uppermost point 12. In various embodiments, such an angle may be at least 60, 65, 70 or degrees (in the exemplary design shown in FIG. 6, the angle is approximately 75 degrees).

As noted earlier herein, in cases in which portions of the frame 4 of the eyeglasses extend along at least an upper portion of the laterally-inward edges of lenses 2 and 3 of the eyeglasses, these portions of the frame will be considered to define (that is, to serve as) the laterally-inward edges of the lenses for the purpose of evaluating the above-recited geometric parameters. That is, in such cases these portions of the frame will provide the surfaces that limit the width of the nose-aperture in these locations and are thus proper to use for such evaluations.

It will be appreciated that the above-recited conditions can provide that the nose-aperture, in particular its upper end, will be generally wide and rounded, rather than being narrow and/or converging to a sharp vertex. This will provide room for the below-described nosepiece to function as disclosed herein.

Nosepiece

Figure 7:
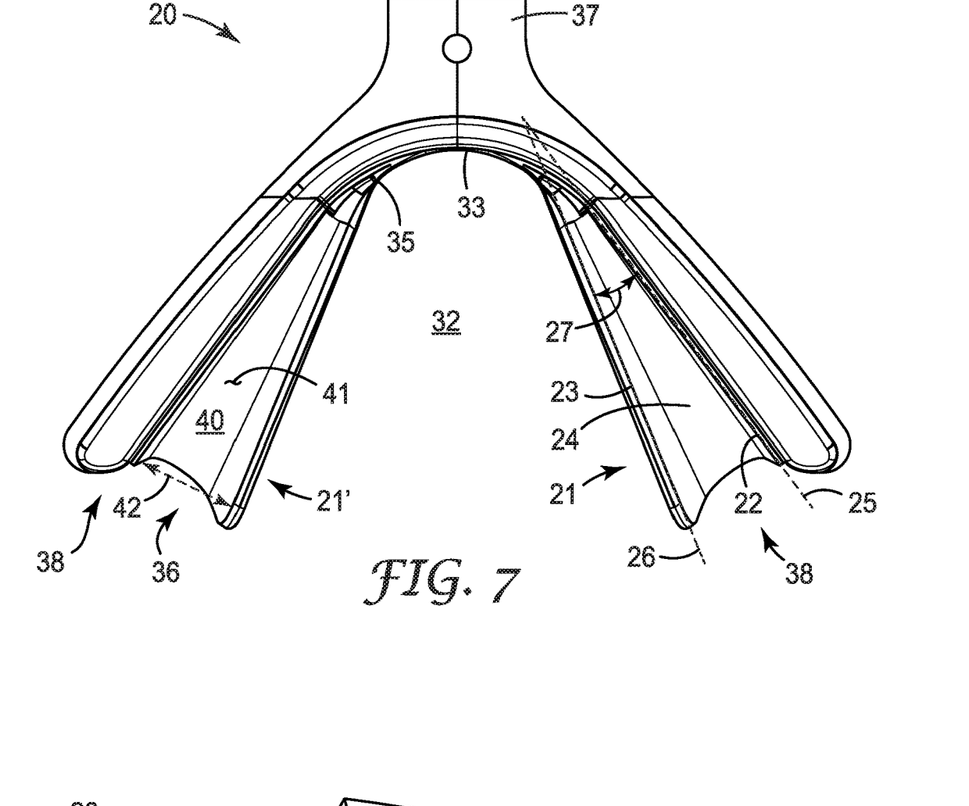
FIG. 7 is a front view of an exemplary nosepiece as disclosed herein.

As shown in exemplary manner in the front and rear views of FIGS. 2 and 3, eyeglasses 1 will comprise a nosepiece 20 that comprises left and right nosepads 21 and 21'. As shown in FIGS. 2 and 3, right and left nosepads 21 and 21' will be laterally spaced apart and will be downwardly laterally diverging, meaning that the left and right nosepads are spaced farther laterally apart from each other in locations nearer to their distal ends 38, as evident from FIG. 3. This spacing and divergence will provide a space 32 configured to accept a wearer's nose, as indicated in FIG. 7, which is an isolated view of an exemplary nosepiece 20. In many convenient embodiments, this may be achieved by providing nosepiece 20 as a generally Y-shaped entity (strictly-speaking, an upside-down Y), with a common upper base 37 from which arms (nosepads) 21 and 21' spread laterally outwardly as they descend.

U-Shaped Cross-Section

As disclosed herein, a nosepad 21 is elongate and will exhibit a generally U-shaped cross-section. As seen in FIG. 7, such a nosepad will comprise laterally-outward elongate sidewall 22 and a laterally-inward elongate sidewall 23, with the sidewalls being connected to each other by an elongate valley floor 24. The sidewalls and the valley floor collectively provide the generally U-shaped cross-section, and collectively define an air gap 40 between the sidewalls as shown in FIG. 7.

It will be understood that by a generally U-shaped cross-section is meant that a general U shape is evident when looking at an elongate nosepad 21 along its long axis. The general U shape is indicated by curved block arrow 45 in FIG. 8, which is a similar view to FIG. 7 but with the nosepiece having been rotated to a view closer to being along the long axis of the nosepad so that the cross-sectional U shape of nosepad 21 is more evident. It is emphasized that the term generally U-shaped is used for convenience of description and does not require, for example, that any portion of the "arms" of the U (that is, sidewalls 22 and 23) must be exactly parallel to each other. Nor does it imply that any portion of the "floor" of the U (that is, valley floor 24) must or must not be planar, or must possess any particular (e.g. symmetric or unsymmetric) curvature. Thus, the term generally U-shaped could also be phrased as, e.g., generally C-shaped, horseshoe shaped, bowl shaped, or parabolic, among other possibilities. All that is necessary is that the nosepad, when viewed along its elongate axis, exhibit features that an ordinary artisan would recognize as being laterally inward and outward sidewalls and a valley floor and that collectively define an air gap between the sidewalls. By definition, the nosepad will comprise an open "top" as indicated by opening 41, opposite valley floor 24, as shown in FIG. 7, rather than being closed off or covered by any kind of wall or partition. Any such nosepad will comprise a single pair of sidewalls and valley floor; thus, such arrangements will be distinguished from e.g. pleated or corrugated arrangements in which a nosepad may include numerous fan-folded segments that can expand or collapse accordion-style.

Figure 9:
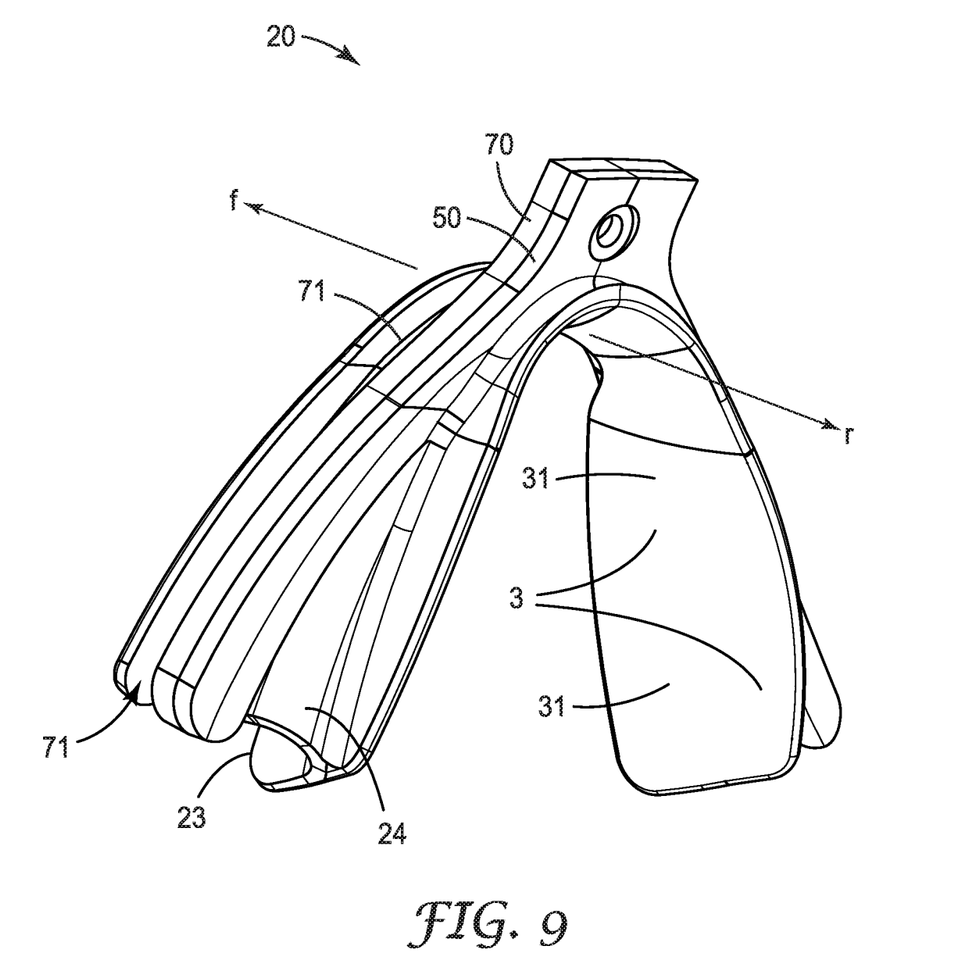
FIG. 9 is an oblique rear view of the nosepiece of FIG. 7.

It is evident from the front and rear views of exemplary nosepads in FIGS. 7 and 9 (as well as in the front and rear views of FIGS. 2 and 3) that in the depicted embodiments, the nosepads 21 comprise a forward-facing U shape. That is, the open end of the U faces forward, away from the wearer's face (as can be seen in FIG. 2), and the closed end of the U (valley floor 24) is oriented rearward, toward the wearer's face as can be seen in FIG. 9. In some embodiments, this arrangement could be reversed, with the open end of the U facing rearward and the closed end (valley floor) facing forward, if desired.

Figure 8:
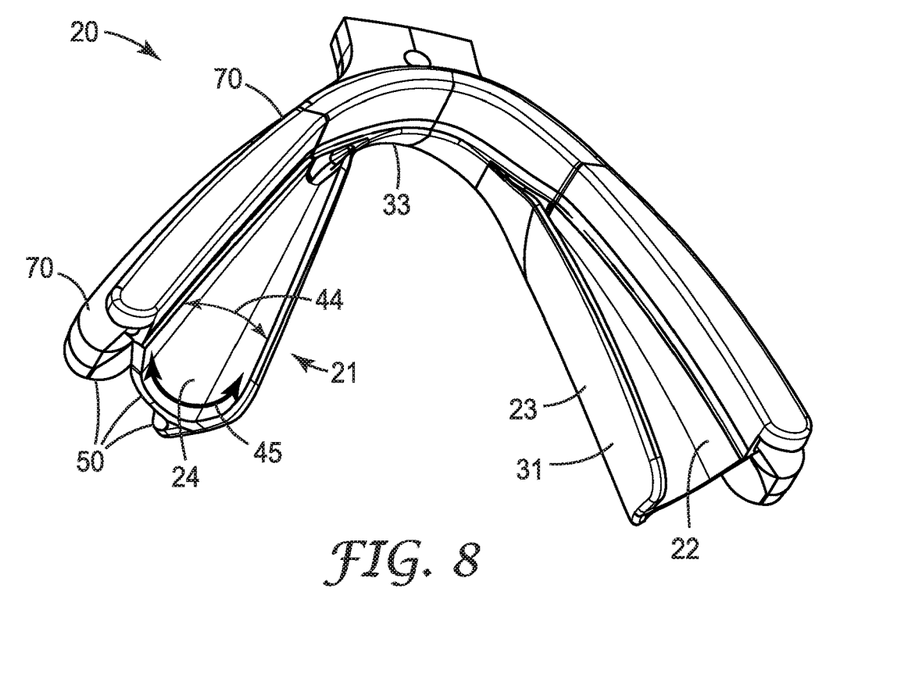
FIG. 8 is an oblique front view of the nosepiece of FIG. 7.

In the absence of any applied force, a nosepad 21 will be in a "resting" or zero-force configuration as shown in FIGS. 7 and 8. This will typically be a fully expanded condition. In response to a force, such a nosepad can deflect by way of laterally-inward sidewall 23 being urged laterally outward toward laterally-outward sidewall 22 in the general manner indicated by arrow 44 in FIG. 8. This will reduce the width 42 of air gap 40 (e.g. at least partially closing the "U", as indicated by arrow 44 in FIG. 8) at least at the location of sidewall 23 that is subjected to the force (e.g., the location of sidewall 23 that comes into contact with a nose or facemask). A larger force will cause a larger deflection of sidewall 23; removal of the force will result (due to the resilience of the material of which the nosepad is made, as discussed below) in sidewall 23 automatically returning back toward its original, "resting" position. The discussion earlier herein of how nosepads 21 can automatically self-adjust to variations in nose size and shape, and the presence or absence of a facemask, can now be readily understood and appreciated. In particular it will be apparent that the sidewalls and valley floor of a nosepad will be reversibly deflectable between a first, undeflected (resting) state in the absence of any force applied thereto, and a variety of second, deflected states in response to various forces applied thereto. The nosepad can reversibly enter a second, deflected state e.g. through the action of a wearer's nose impinging on the laterally-inward sidewall of the nosepad, with the extent of the deflection depending on the forces encountered.

In other words, the herein-described nosepads can remain in a relatively undeflected (e.g. resting) configuration in order to accommodate a relatively narrow nose of an unmasked wearer, but can deflect a considerable amount to accommodate the extra space occupied by a facemask. That is, the nosepads can deflect so as to occupy less space when used with a wide nose and/or in the presence of a facemask, but can fully deploy to fill any gap between the wearer's nose and the edges of the eyeglass lenses, when used with a narrow nose and/or in the absence of a facemask. In this sense the nosepads may expand and contract in a manner reminiscent of a flexible bellows.

The material of which at least the laterally-inward sidewall 23 and valley floor 24 of nosepad 21 are made, should be sufficiently compliant and resilient to achieve the effects described herein. In some embodiments, the laterally-outward sidewall 22 may similarly be compliant and resilient. In many embodiments, all such items may be portions of a single, integral, molded piece chosen of a material that exhibits the appropriate compliance and resilience.

It has been found that the Shore Hardness (A scale, at 21 degrees C.) is an appropriate parameter for characterizing the resilience and compliance of the nosepad material. Thus, a nosepad (i.e., comprising sidewalls and a valley floor) as disclosed herein will be made of a material that exhibit a Shore A hardness (at 21 degrees C.) of 70 or less. In various embodiments, the material may exhibit a Shore A hardness of at most 60 or 50. In further embodiments, the material may exhibit a Shore A hardness of at least 30, 35, 45, or 55. (Various suitable materials are mentioned later herein.)

As noted earlier, in many embodiments elongate nosepads 21 will be laterally diverging. (Often, as is evident from FIG. 2, in many embodiments each elongate nosepad 21 will exhibit a long axis that is generally, or substantially, aligned with the overall slope of the laterally-inward terminal edges of the eyeglasses lenses.) Beyond this, in some embodiments nosepads 21 may be upwardly tapered. With reference to FIG. 7, by upwardly tapered is meant that a width of the elongate air gap at an upper end 35 of the nosepad (meaning an end that is proximal to upper base 37 of nosepiece 20) is less than half of the width of the air gap at a lower end 38 of the nosepad. By the lower end 38 is meant a terminal end of the nosepad that is distal to the base 37; the width 42 of the airgap at lower end 38 is indicated in FIG. 7. In such embodiments, such an air gap may thus be a downwardly-diverging gap, meaning that the width of the air gap increases as the lower, distal end 38 of the nosepad is approached. Tapering the nosepads in this manner can provide further ability for the nosepad to adjust to greater and lesser extents at locations where such ability may or may not be most needed.

The taper of a nosepad may be characterized in terms of a taper angle 27, which, as indicated in FIG. 7, is the angle between lines 25 and 26 that are superimposed on the surfaces of the laterally outward and inward sidewalls. In various embodiments, such a taper angle may be at least 5, 10, or 15 degrees; in further embodiments, such a taper angle may be at most 30, 25, or 20 degrees. (In the exemplary illustration of FIG. 7, the taper angle is approximately 15 degrees.)

As evident in FIG. 7, in some embodiments, the width 42 of air gap 40 may go to zero (that is, air gap 40 may disappear completely) at upper end 35 of nosepad 21. In other words, at location 35 the laterally inward sidewall 23 may merge with the laterally outward sidewall 22. Thus in some embodiments, an upper "bridge" portion 33 of nosepiece 20 may not necessarily have any ability to reversibly deflect, since, typically, little or no self-adjustability at that location may be needed. Also, in many embodiments nosepad 21 will terminate at its lower end 38 in an open-ended manner. That is, the lower (distal) end of air gap 40 will comprise an opening 36 as shown in FIG. 7, rather than being e.g. closed off by a wall or partition. This can preserve the maximum ability of the lower end of the nosepad to deflect as needed.

In some embodiments, the depth 43 of an air gap 40 (most easily seen in FIG. 12) may decrease commensurately with a decrease in the width of the air gap. In other words, in such embodiments, a tapered nosepad may exhibit a decrease in both the width and depth of air gap 40 as the nosepad is traversed upward and laterally inward. In various embodiments, the depth of the air gap at the upper end of the nosepad may be less than ⅔, ½, or ⅓ of the depth of the air gap at the lower end of the nosepad. As noted above, in some embodiments the air gap may disappear completely toward the upper end of the nosepad. A nosepad that is tapered in this general manner so as to have an air gap with a width and depth that are greatest at a distal end of the nosepad and that decrease and e.g. vanish at the proximal end of the nosepad, may exhibit an appearance (as most evident e.g. in FIGS. 2, 7 and 8) that is somewhat similar to half of a "Rogallo" wing.

As noted earlier, nosepads 21 will provide nose-contact surfaces 31 that are the surfaces that are configured to actually touch the nose (or facemask, when present). The viewing angle of FIG. 9 allows provides an excellent view of nose-contact surfaces 31 of a nosepad. As evident from FIG. 9, in some embodiments the nose-contact surfaces can have a larger area at locations lower down the nosepad and can be somewhat narrowed as the bridge portion 33 of the nosepad is approached (this is most evident in the bottom view of FIG. 14).

Cushioning Piece and Support Piece

In some embodiments, a nosepiece 20 may be provided by two separately-made pieces that are attached to each other. One such arrangement is depicted in exemplary embodiment in the oblique front exploded view of FIG. 10. In such embodiments, nosepiece 20 comprises a first, cushioning piece 50, which provides the above-described left and right nosepads 21, including the sidewalls, valley floors, nose-contact surfaces and so on. In various embodiments, at least the sidewalls and valley floors will be made of a compliant, resilient material as described previously (in many convenient embodiments, the entirety of piece 50 may be made of such material). Cushioning piece 50 is attached to a support piece 70. Typically, cushioning piece 50 is non-detachably attached to support piece 70. This can be done through any suitable attachment means, e.g. mechanical fastening, solvent bonding, ultrasonic bonding, adhesive bonding, and so on. In some embodiments, support piece 70 may be made (e.g. by injection molding) and cushioning piece 50 may be overmolded onto support piece 70.

Cushioning piece 50 may be made of any suitable material that exhibits the requisite compliance and resilience, e.g. as characterized by a Shore A hardness as discussed earlier herein. Suitable materials may be chosen from e.g. plasticized PVC, silicones, polyurethanes (e.g. the material available under the trade designation SORBOTHANE), synthetic rubbers, thermoplastic elastomers (TPEs), and the like. It will be appreciated that in the present arrangements, the desired compliance and resilience can be achieved primarily by bending of the material (e.g., the portion of the material that makes up the sidewalls and/or valley floors of the nosepads), rather than by compression/densification of the material. So, it may not be necessary for this material to be compressible, i.e. densifiable, in the manner of a compressible polymeric foam such as a polyurethane foam. Thus, in various embodiments, the material of which cushioning piece (and, in some embodiments, the entire nosepiece 20) is made, may be a "dense" (i.e. non-cellular and in particular non-foam) material with a density of at least 0.8, 0.9, 0.95, or 1.0 g/cc.

Support piece 70 provides physical support and mechanical integrity to nosepiece 20; in some embodiments it may provide a mechanism for nosepiece 20 to be attached to eyeglasses 1. Support piece need not necessarily be made of a compliant, resilient material; rather, in various embodiments, support piece 70 may be made of a somewhat rigid thermoplastic injection molding material such as e.g. polycarbonate or nylon. In various embodiments, such a material may exhibit a Shore A hardness of at least 70, 80, 90, or 100.

In some embodiments cushioning piece 50 and support piece 70 may both be generally Y-shaped pieces (e.g. as in FIG. 10) that fit into the flared nose-aperture of the eyeglasses. In many embodiments, it will be convenient to join these pieces together to form the nosepiece 20, and to then attach the thus-formed nosepiece to the eyeglasses (rather than installing the individual pieces into the eyeglasses separately).

Figure 10:
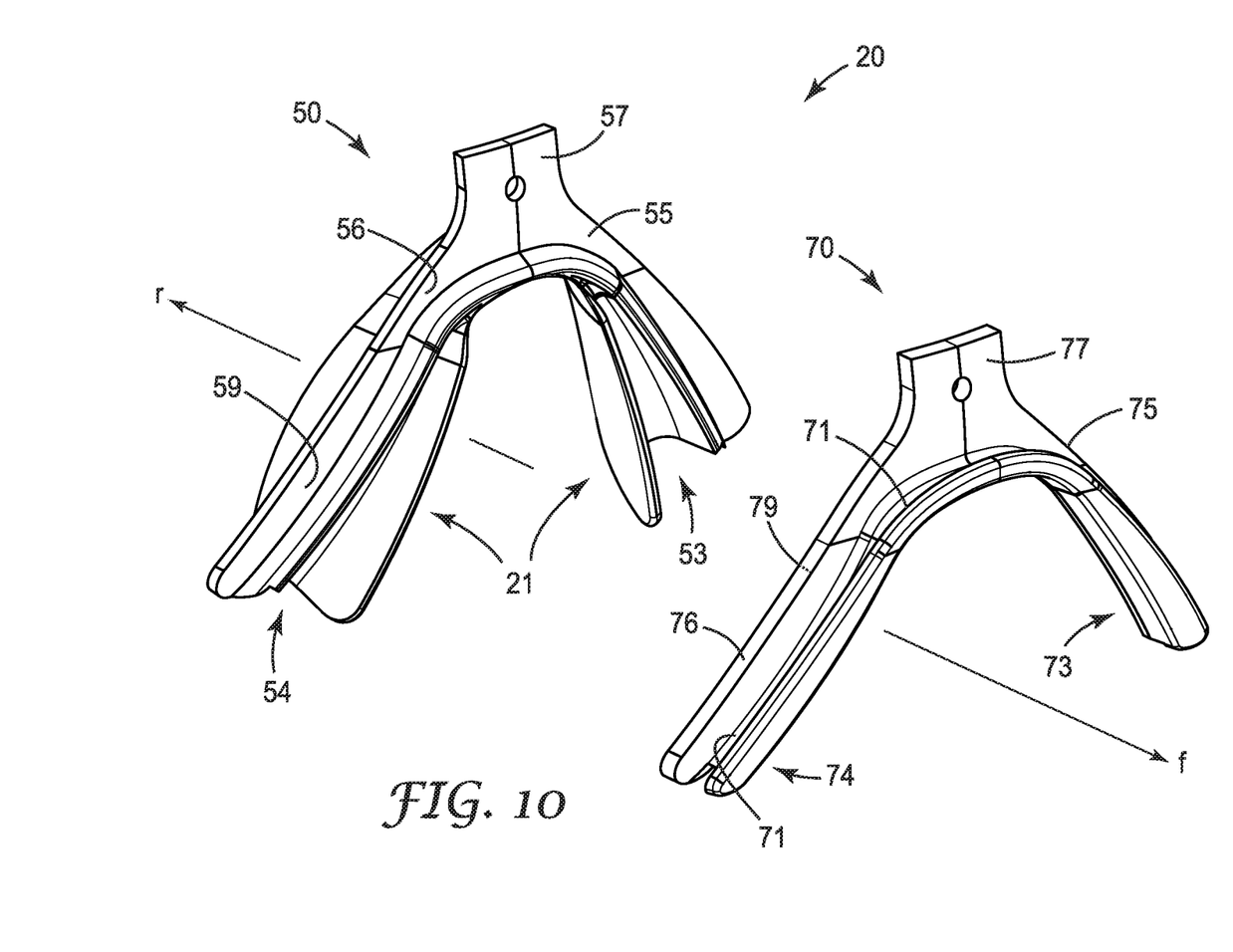
FIG. 10 is an exploded, oblique front view of the nosepiece of FIG. 7, showing an exemplary cushioning piece and an exemplary support piece of the nosepiece.

In some embodiments, the generally Y-shaped cushioning piece 50 comprises a left elongate leg 53 and a right elongate leg 54. The generally Y-shaped second, support piece 70 may similarly comprise a left elongate leg 73 and a right elongate leg 74. The legs of both pieces can be similarly sized and shaped so that when the cushioning piece and the support piece are attached to each other, the left elongate leg of the cushioning piece is in contact with the left elongate leg of the support piece, and the right elongate leg of the cushioning piece is in contact with the right elongate leg of the support piece. In particular embodiments, cushioning piece 50 may comprise left and right flanges 55 and 56 that comprise a major forward surface 59, while support piece 70 may comprise left and right flanges 75 and 76 that comprise a major rearward surface 79, all as shown in FIG. 10. When the cushioning piece 50 and the support piece 70 are joined together, major surface 59 of piece 50 may abut, and contact, major surface 79 of piece 70.

In some embodiments, cushioning piece 50 may comprise an upper base 57, and support piece 70 may similarly comprise an upper base 77. When the two pieces are joined together to form nosepiece 20, bases 57 and 77 may collectively form the previously mentioned upper base 37 of nosepiece 20. Nosepiece may be attached to eyeglasses 1, e.g. to a portion of frame 4 of eyeglasses 1, via any suitable method. In the depicted embodiment, bases 57 and 77 have aligned through-holes through which a screw or similar device can be inserted to attach base 37 to bridge portion 5 of frame 4 of eyeglasses 1. In general, any method of attachment, whether by the use of mechanical fastening such as with one or more screws, clips, deformable tabs, etc.; or, chemical bonding such as solvent bonding or adhesive bonding; or, thermal bonding such as e.g. ultrasonic bonding or high frequency welding, can be used to attach the nosepiece to the eyeglasses. In various embodiments, the attachment can be permanent or the nosepiece may be detachable from the eyeglasses. In some embodiments, the nosepiece may be snap-fitted into place in the nose-aperture, with or without any additional bonding or mechanical fastening being performed.

In some embodiments (regardless of the mechanism of joining or attachment of the nosepiece to the eyeglasses), support piece 70 may comprise an elongate notch 71 (most easily seen in FIGS. 9 and 10) that extends along at least a portion of the arms of the Y-shaped support piece. Such a notch 71 can be configured so that when support piece 70 (as part of nosepiece 20) is fitted into flared nose-aperture 10 and attached to eyeglasses 1, portions of laterally-inward terminal edges 7 and 8 of left and right lenses 2 and 3 will be received into elongate notch 71. This may additionally stabilize the nosepiece in place.

With the above discussions, it can now be appreciated that nosepiece 20 as shown in FIGS. 1-4 and 7-9 is a two-piece nosepiece of the general type described above. In various of these figures, the individual pieces 50 and 70 are indicated.

Figure 11:
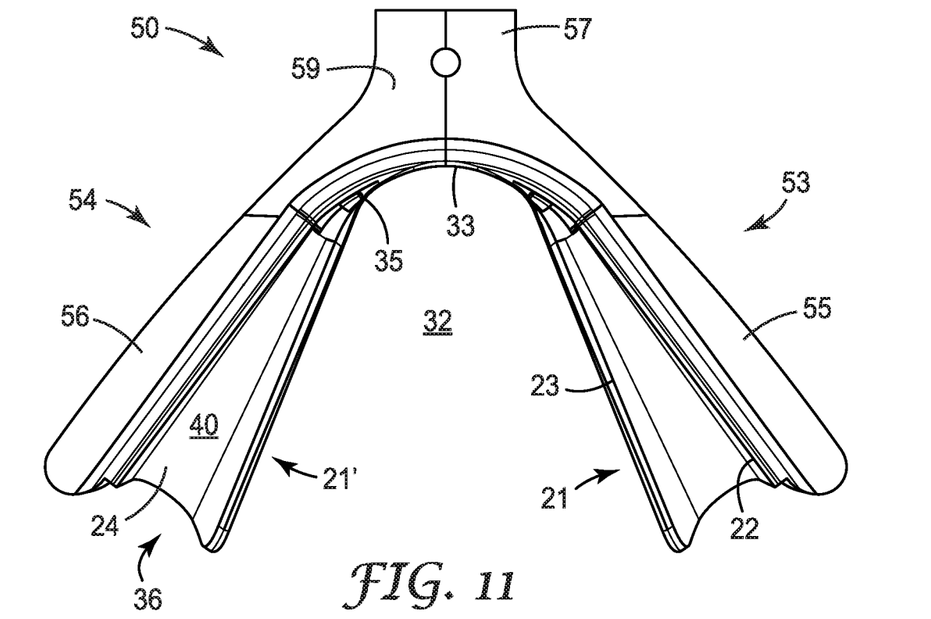
FIG. 11 is a front view of the cushioning piece of FIG. 10.
Figure 12:
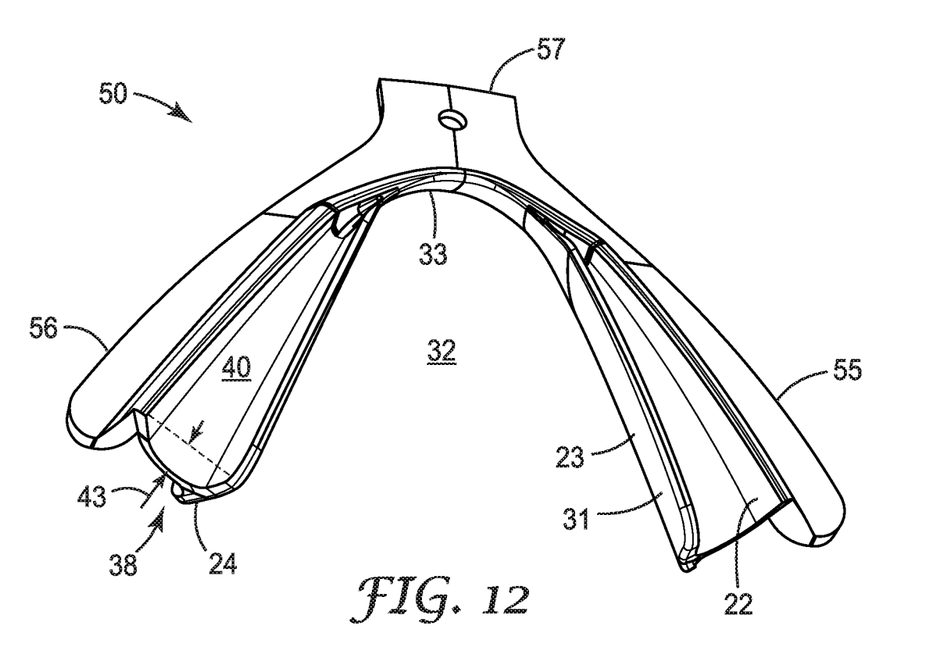
FIG. 12 is an oblique front view of the cushioning piece of FIG. 11.
Figure 13:
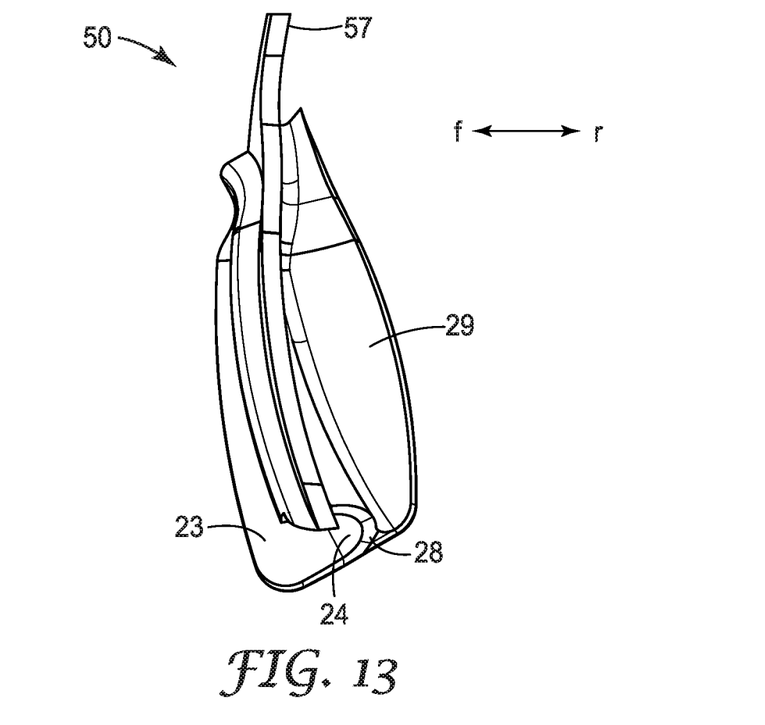
FIG. 13 is a side view of the cushioning piece of FIG. 11.
Figure 14:
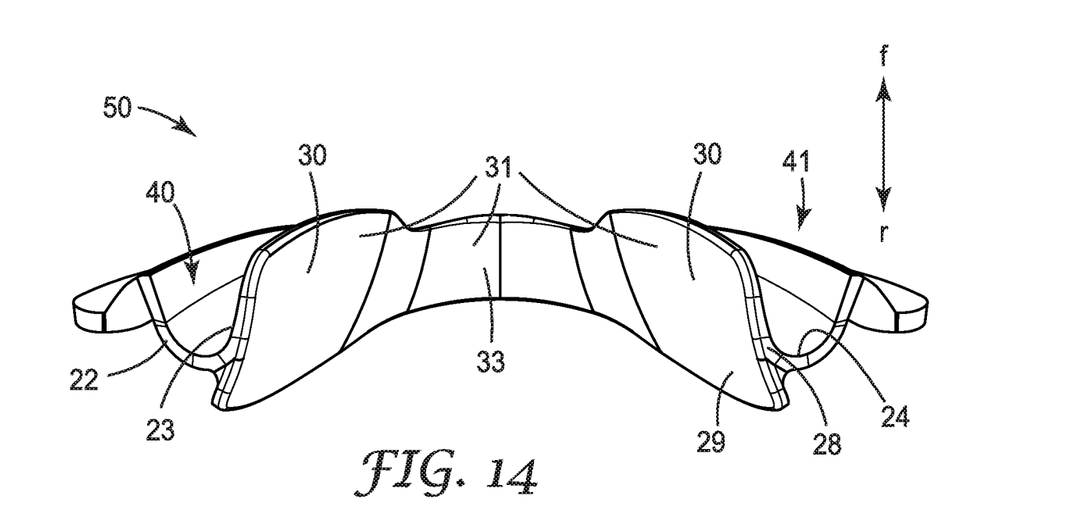
FIG. 14 is a bottom view of the cushioning piece of FIG. 11.

FIGS. 11-14 depict cushioning piece 50 in isolated view (with support piece 70 omitted), so that further features of cushioning piece 50 can be more easily seen. FIGS. 11 and 12 are front and oblique-front views; FIGS. 13 and 14 are respectively side and bottom views. As evident from these Figures, cushioning piece 50 provides nosepads 21 and the components thereof (i.e., the sidewalls, valley floor, contact surfaces, and so on).

Figure 15:
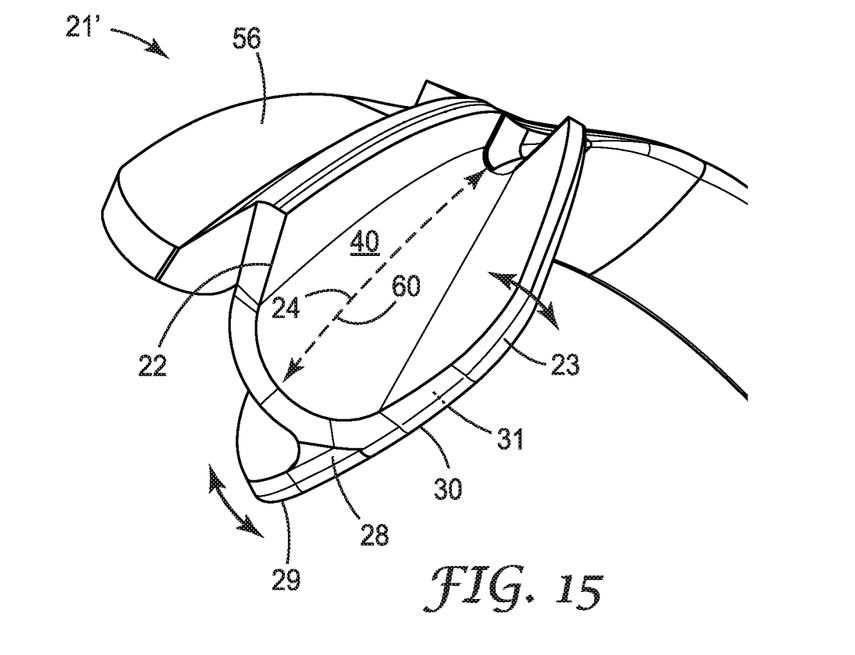
FIG. 15 is a view of an exemplary nosepad of the cushioning piece of FIG. 11.
Figure 16:
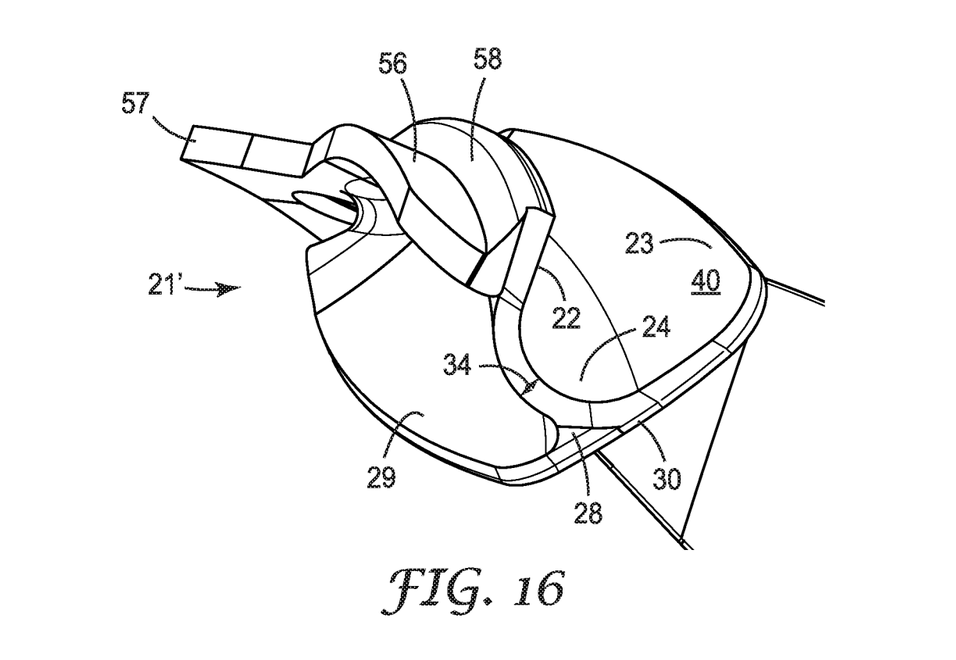
FIG. 16 is another view of the exemplary nosepad of FIG. 15.

FIGS. 15 and 16 are magnified views of a single elongate nosepad 21 (in this case, a right nosepad 21'), from the open (forward) side of the U-shaped nosepad, looking along the long axis of the nosepad at an oblique angle. The view of FIG. 16 is shifted slightly so that certain features can be more easily seen, as discussed below. The long axis of elongate nosepad 21 is indicated by dashed arrow 60 in FIG. 15; this makes it readily apparent why the sidewalls, valley floor, and nosepad as a whole are characterized as elongate, since they all extend along long axis 60. In FIGS. 15 and 16, various features and arrangements already discussed earlier herein can be seen—the cross-sectional generally U shape of the nosepad when viewed along the long axis, the fact that the nosepad is tapered so that the width and depth of the air gap 40 decreases as the proximal end of the nosepad is approached, and so on. However, another arrangement is revealed in these figures.

Laterally-inward elongate sidewall 23 of elongate nosepad 21 provides a nose-contact "plate" 30 that comprises a nose-contact surface 31, as described earlier herein. As seen in FIG. 15, elongate valley floor 24 meets elongate laterally-inward sidewall 23 at an elongate junction 28. FIG. 15 further reveals that in addition to the presence of laterally-inward sidewall 23, in this exemplary design an elongate secondary flange 29 is present, that meets sidewall 23 at elongate junction 28 and that extends away from junction 28 in a generally opposite direction from sidewall 23. Thus in the illustrated embodiment, nose-contacting "plate" 30 is provided by elongate sidewall 23 and elongate secondary flange 29 acting in combination. This can also be seen in the bottom view of FIG. 14. (It is noted that the term "plate" is used for convenience in view of the plate-like appearance of item 30 and does not signify that the item must be rigid; in fact, "plate" 30 will be compliant and resilient as described herein.) Secondary flange 29 combines with laterally-inward sidewall 23 to provide a resilient, conformable nose-contact plate 30 with increased total surface area available for contact with the nose, and thus can provide enhanced comfort.

The present work has revealed another, more subtle function of such an arrangement. It has been found that elongate junction 28 can serve as a pivot that can provide a rotation axis about which plate 30 formed by sidewall 23 and flange 29 can partially rotate, as indicated by the two curved arrows in FIG. 15. This rotation axis will be at least generally aligned with (parallel to) the long axis 60 of the elongate nosepad. Thus, junction 28 can act as a fulcrum about which plate 30 can partially rotate in the general manner of a see-saw. This can provide that when eyeglasses 1 are donned by a wearer, flange 29 (which is on the rearward side of the eyeglasses, facing toward the wearer) may contact the wearer's nose and be urged laterally outward. This can cause plate 30 to rotate thus causing sidewall 23 to rotate laterally inward, toward an adjacent area of the wearer's nose. This can allow nosepad 21 to more effectively fill any gap between the laterally-inward edges of the lenses of the eyeglasses and the wearer's nose.

FIG. 16 illustrates still another arrangement that may be used. As already noted, a nosepad may comprise an elongate flange 56 to which laterally-outward elongate sidewall 22 is connected. In some embodiments, elongate sidewall 22 may extend directly from elongate flange 56. However, in some embodiments, an elongate rib 58 may extend e.g. generally forwardly from elongate flange 56, in the general manner shown in FIG. 16. In some embodiments, elongate sidewall 22 may extend from some portion (e.g., from a forward portion) of elongate rib 58; such arrangements may, for example, may add to the depth of the air gap of the U-shaped nosepad or may otherwise enhance the compliance and resilience of the nosepad.

FIG. 16 also provides an indication of the thickness 34 of valley floor 24. This thickness may be any suitable value, and may be chosen in combination with the resilience and flexibility of the material of which the nosepad is made. In various embodiments, the average thickness of valley floor 24, of laterally-inward sidewall 23, and/or of laterally-outward sidewall 22, may be at least 0.10, 0.20, or 0.30 mm. In further embodiments, this average thickness may be at most 1.0, 0.80, 0.60, or 0.40 mm. In some embodiments, the thickness of the sidewalls may be relatively similar to that of the valley floor, as in FIG. 16. The thickness may be constant or may vary (in particular, the thickness of sidewall 22 may decrease slightly toward the terminal edges of the sidewall).

Other features or arrangements may be used in order to tailor the resilience and compliance of the nosepiece. For example, one or more support ribs may be spaced along the elongate length of valley floor 24 and may extend between the sidewalls in a manner that purposefully alters the local compliance or resistance to bending of the sidewalls, at various locations along the elongate length of the nosepiece. In some embodiments, one or more notches or cutouts may be provided e.g. in laterally-inward sidewall 23, to affect the local compliance or resistance to bending. In some embodiments, multiple such notches may be spaced along the elongate length of sidewall 23. In some particular embodiments, a notch or cutout may be provided between the bridge portion 33 of nosepiece 20, and laterally-inward sidewall 23.

In various embodiments, the maximum width of air gap 40 (e.g. width 42 at the distal end 38 of nosepad 21, as indicated in FIG. 7) may be at least 2, 3 or 4 mm. In further embodiments, the maximum width may be at most 10, 8, 6 or 5 mm. In various embodiments, the maximum depth of air gap 40 (e.g. depth 43 as indicated in FIG. 12, may be at least 2, 3 or 4 mm. In further embodiments, the maximum depth may be at most 10, 8, 6 or 5 mm.

It will be appreciated that numerous variations are encompassed within the scope of the above-described arrangements. As noted, a nosepiece may be permanently, or detachably, attached to the eyeglasses, in any suitable manner. Although the nosepiece is intended to fit under a wide range of conditions, in some embodiments eyeglasses may be provided as a kit including a herein-disclosed self-adjustable nosepiece, and a non-self-adjustable nosepiece, that may be swapped in various circumstances. For example, the herein-disclosed nosepiece may be installed for a long term period in which the wearer is intermittently wearing a facemask, and the non-self-adjustable nosepiece may be installed when the wearer goes for long times (e.g. days or weeks) without wearing a facemask. Of course, any such non-self-adjustable nosepiece should be designed in view of the flared nose-aperture of the eyeglasses. As noted, a nosepiece may be oriented with the open end of the U facing forward, away from the user's face, or rearward, toward the user's face. The nosepiece may be available in various colors.

Figure 17:
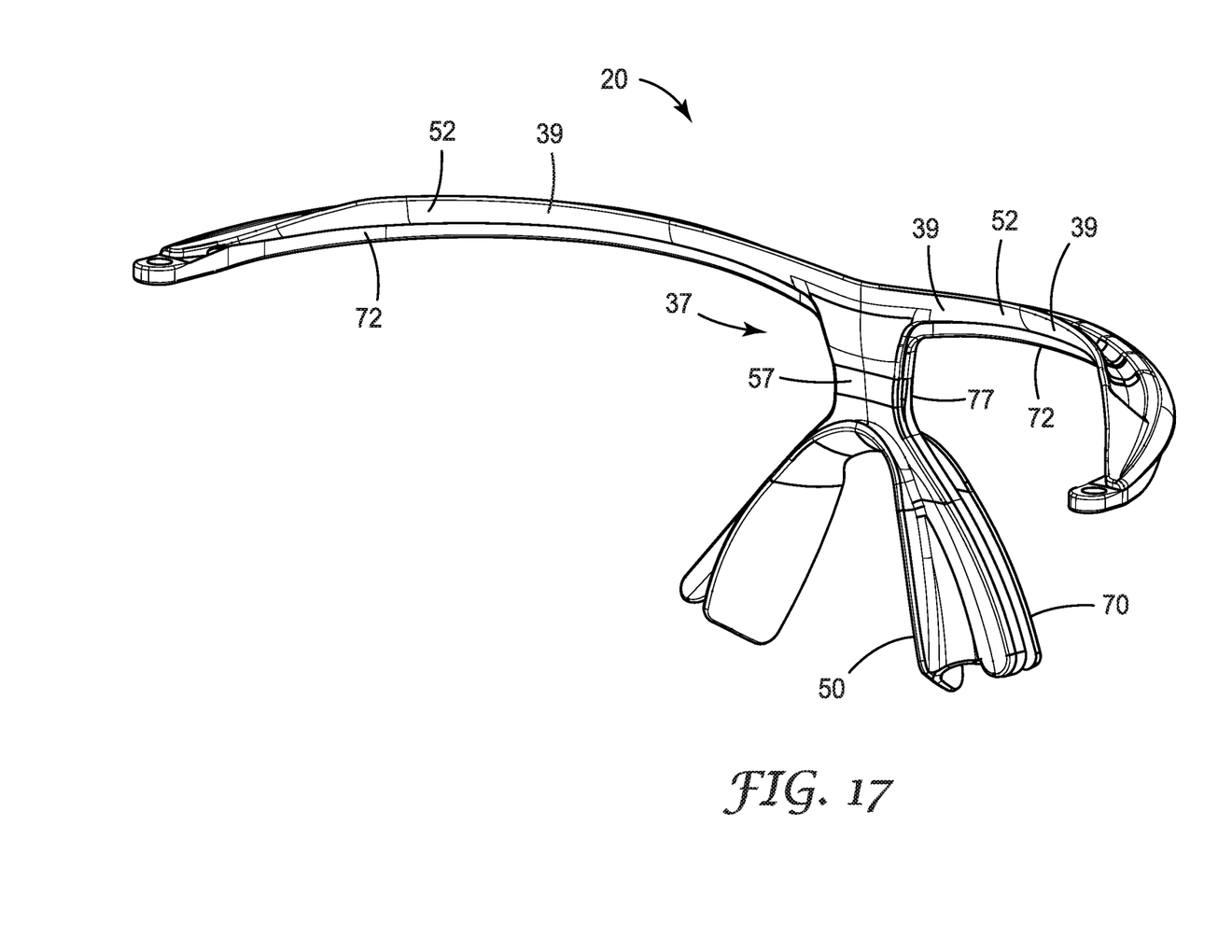
FIG. 17 is an exemplary illustration of an integrated nosepiece/brow guard.

In some embodiments, the nosepiece (e.g. at least a first, cushioning piece thereof) may extend along the upper edges of the lenses to provide a resilient brow guard or cushion. One such arrangement of this general type is illustrated in exemplary manner in FIG. 17 (which is an oblique rear view with the lenses and frame of the eyeglasses omitted). FIG. 17 illustrates a design in which a herein-disclosed nosepiece is integrated with a brow guard 39. Such a brow guard (which may sometimes be referred to e.g. as a brow bar, brow pad, or brow cushion) may comprise two (left and right) compliant portions 52 that face generally rearward, toward the brow of the wearer. In the illustrated design, compliant portions 52 integrally extend laterally outward from upper base 57 of cushioning piece 50. In the illustrated design, portions 72 similarly integrally extend laterally outward from upper base 77 of support piece 70. Portions 52 and 72 may be joined together if desired, by any suitable means, so that portions 72 of support piece 70 provide mechanical support for portions 52 of cushioning piece 50. In some embodiments, portions 72 may be shorter or even omitted, e.g. with portions 52 of cushioning piece 50 being attached directly to a portion of the frame of the eyeglasses.

A nosepiece 20 as disclosed herein may be used with any type of eyeglasses, including but not limited to eyeglasses (spectacles) configured for vision correction, eyeglasses configured for physical protection (e.g. safety glasses), eyeglasses configured for protection from radiation (e.g. sunglasses or eyeglasses for laser protection) and combinations of any of these (e.g. eyeglasses for welding). Examples of specific types of eyeglasses with which such nose supports may be used include those for nearsightedness, those for farsightedness, reading glasses, computer glasses, anti-glare glasses, bifocal and trifocal glasses, progressive-lens glasses, 3-D glasses, and so on. As noted, such eyeglasses may be of any suitable design, including but not limited to designs in which a frame of the eyeglasses fully or partially surrounds the lenses of the eyeglasses, and those in which the frame consists essentially of only a bridge portion.

It will be apparent to those skilled in the art that the specific exemplary elements, structures, features, details, configurations, etc., that are disclosed herein can be modified and/or combined in numerous embodiments. All such variations and combinations are contemplated by the inventor as being within the bounds of the conceived invention, not merely those representative designs that were chosen to serve as exemplary illustrations. Thus, the scope of the present invention should not be limited to the specific illustrative structures described herein, but rather extends at least to the structures described by the language of the claims, and the equivalents of those structures. Any of the elements that are positively recited in this specification as alternatives may be explicitly included in the claims or excluded from the claims, in any combination as desired. Any of the elements or combinations of elements that are recited in this specification in open-ended language (e.g., comprise and derivatives thereof), are considered to additionally be recited in closed-ended language (e.g., consist and derivatives thereof) and in partially closed-ended language (e.g., consist essentially, and derivatives thereof). To the extent that there is any conflict or discrepancy between this specification as written and the disclosure in any document that is incorporated by reference herein but to which no priority is claimed, this specification as written will control.

What is claimed is:

1. Eyeglasses comprising:
left and right lenses and a frame that supports the left and right lenses and that comprises a bridge portion that connects the left and right lenses, with at least the bridge portion of the frame and laterally-inward terminal edges of the left and right lenses being configured to define a flared nose-aperture;
and,
a nosepiece that is positioned in the flared nose-aperture and is connected to the eyeglasses,
wherein the nosepiece comprises a left nosepad and a right nosepad, the nosepads being spaced laterally apart and downwardly laterally diverging to accommodate a nose of a wearer of the eyeglasses and each nosepad being elongate and generally U-shaped in cross-section and being made of a compliant material with a Shore A hardness of between 30 and 70;
wherein each elongate nosepad comprises a laterally-outward elongate sidewall and a laterally-inward elongate sidewall, the elongate sidewalls being connected to each other by an elongate valley floor so that the elongate sidewalls and the elongate valley floor collectively provide the generally U-shaped cross section, and wherein the elongate sidewalls and the elongate valley floor collectively define an elongate air gap between the elongate sidewalls;
and,
wherein for each elongate nosepad, the elongate valley floor meets the laterally-inward elongate sidewall at an elongate junction; and, wherein an elongate secondary flange extends from the elongate junction in a generally opposite direction from the laterally-inward elongate sidewall, so that the laterally-inward elongate sidewall and the secondary flange collectively provide a resilient, conformable nose-contact plate.

2. The eyeglasses of claim 1 wherein each elongate nosepad exhibits a forward-facing U-shape with an open end of the U facing forward, away from the wearer's face, and with the elongate valley floor of the nosepad being oriented rearward, toward the wearer's face.

3. The eyeglasses of claim 1 wherein the elongate junction serves as a pivot that provides a rotation axis about which the resilient, conformable nose-contact plate can partially rotate, the rotation axis being at least generally aligned with the long axis of the elongate nosepad.

4. The eyeglasses of claim 1 wherein the nosepiece comprises first, cushioning piece that comprises the left and right nosepads and is made of a compliant material with a Shore A hardness of between 30 and 70; and, a second, support piece, to which the first, cushioning piece is non-detachably attached.

5. The eyeglasses of claim 4 wherein the first, cushioning piece is a single, integral, molded piece that is made of a compliant material with a Shore A hardness of between 40 and 60 and wherein the second, support piece is a single, integral, molded piece that is made of a material with a Shore A hardness of at least 80.

6. The eyeglasses of claim 4 wherein the first, cushioning piece, and the second, support piece, are each a generally Y-shaped piece that fits into the flared nose-aperture of the eyeglasses, with the nosepiece being attached to the eyeglasses by way of the second, support piece and with all contact surfaces of the nosepiece being provided by the first, cushioning piece.

7. The eyeglasses of claim 6 wherein the second, support piece comprises an elongate notch that is configured so that when the second, support piece is fitted into the flared nose-aperture and attached to the eyeglasses, at least a portion of laterally-inward terminal edges of the left and right lenses are received into the elongate notch of the second, support piece.

8. The eyeglasses of claim 6 wherein the generally Y-shaped first, cushioning piece comprises a left elongate leg and a right elongate leg, wherein the generally Y-shaped second, support piece comprises a left elongate leg and a right elongate leg, and wherein when the first, cushioning piece and the second, support piece are non-detachably attached to each other, the left elongate leg of the first, cushioning piece is in contact with the left elongate leg of the second, support piece, and the right elongate leg of the first, cushioning piece is in contact with the right elongate leg of the second, support piece.

9. The eyeglasses of claim 8 wherein for each nosepad, a laterally-outward elongate sidewall of the first, cushioning piece is connected to an elongate leg of the first, compliant piece.

10. The eyeglasses of claim 1 wherein any portion of the flared nose-aperture that is less than 20 mm wide is bounded by lower and/or laterally-inward edges of the bridge portion of the frame and/or by laterally-inward terminal edges of the left and right lenses of the left or right lenses, that are all oriented at an angle that is at least 30 degrees away from a vertical axis of the eyeglasses.

11. The eyeglasses of claim 1 wherein any portion of the flared nose-aperture that is less than 10 mm vertically below an uppermost boundary of the flared nose-aperture is bounded by lower and/or laterally-inward edges of the bridge portion and/or by laterally-inward terminal edges of the left or right lenses, that are all oriented at an angle that is at least 30 degrees away from a vertical axis of the eyeglasses.

12. The eyeglasses of claim 1 wherein the flared nose-aperture of the eyeglasses is upwardly bounded by the bridge portion of the frame and/or by laterally-inward terminal edges of the left and right lenses, so as to exhibit an upper boundary with a radius of curvature of at least 10 mm.

13. The eyeglasses of claim 1 wherein laterally-inward terminal edges of the left and right lenses are oriented at an angle of at least 60 degrees relative to each other.

14. The eyeglasses of claim 1 wherein the frame, including the bridge portion, and the left and right lenses, are all portions of a single, integral molded piece, to which right and left temple arms are attached to provide the eyeglasses.

15. Eyeglasses comprising:
left and right lenses and a frame that supports the left and right lenses and that comprises a bridge portion that connects the left and right lenses, with at least the bridge portion of the frame and laterally-inward terminal edges of the left and right lenses being configured to define a flared nose-aperture;
and,
a nosepiece that is positioned in the flared nose-aperture and is connected to the eyeglasses,
wherein the nosepiece comprises a left nosepad and a right nosepad, the nosepads being spaced laterally apart and downwardly laterally diverging to accommodate a nose of a wearer of the eyeglasses and each nosepad being elongate and generally U-shaped in cross-section and being made of a compliant material with a Shore A hardness of between 30 and 70;

wherein each elongate nosepad comprises a laterally-outward elongate sidewall and a laterally-inward elongate sidewall, the elongate sidewalls being connected to each other by an elongate valley floor so that the elongate sidewalls and the elongate valley floor collectively provide the generally U-shaped cross section, and wherein the elongate sidewalls and the elongate valley floor collectively define an elongate air gap between the elongate sidewalls;
and,
wherein each elongate nosepad is upwardly tapered so that a width of the elongate air gap at an upper end of the elongate air gap is less than half a width of the elongate air gap at a lower end of the elongate air gap.

16. The eyeglasses of claim 15 wherein each elongate nosepad exhibits a taper angle, defined by an angle between the laterally-outward elongate sidewall and the laterally-inward elongate sidewall, of from 5 degrees to 25 degrees.

17. The eyeglasses of claim 15 wherein for each elongate nosepad, a depth of the elongate air gap at the upper end of the nosepad is less than ½ of a depth of the elongate air gap at the lower end of the nosepad.

* * * * *

UNITED STATES PATENT AND TRADEMARK OFFICE
CERTIFICATE OF CORRECTION

| | | |
|---|---|---|
| PATENT NO. | : 12,353,061 B2 | Page 1 of 1 |
| APPLICATION NO. | : 18/026491 | |
| DATED | : July 8, 2025 | |
| INVENTOR(S) | : Laurent Froissard | |

It is certified that error appears in the above-identified patent and that said Letters Patent is hereby corrected as shown below:

In the Claims

<u>Column 14</u>
Line 51, In Claim 10, before "left and right lenses" delete "of the left or right lenses,", therefor Signed and Sealed this
Ninth Day of December, 2025

John A. Squires
*Director of the United States Patent and Trademark Office*